United States Patent [19]

Mokry

[11] Patent Number: 4,944,735
[45] Date of Patent: Jul. 31, 1990

[54] SHAPED NAPKIN WITH ELASTICIZED EDGES

[75] Inventor: Patti J. Mokry, Menasha, Wis.

[73] Assignee: Kimberly-Clark Corporation, Neenah, Wis.

[21] Appl. No.: 843,332

[22] Filed: Mar. 24, 1986

Related U.S. Application Data

[63] Continuation of Ser. No. 581,945, Feb. 21, 1984, abandoned.

[51] Int. Cl.$^5$ .............................................. A61F 13/16
[52] U.S. Cl. ................................. 604/385.2; 604/366
[58] Field of Search ............... 604/385.1, 385.2, 370, 604/366

[56] References Cited

U.S. PATENT DOCUMENTS

| | | | |
|---|---|---|---|
| 3,371,668 | 3/1968 | Johnson . | |
| 3,860,003 | 1/1975 | Buell . | |
| 4,226,238 | 10/1980 | Bianco . | |
| 4,324,245 | 4/1982 | Mesek et al. | 604/385.2 |
| 4,324,246 | 4/1982 | Mallane et al. | 604/370 |
| 4,326,528 | 4/1982 | Ryan et al. . | |
| 4,337,771 | 7/1982 | Pieniak et al. . | |
| 4,352,355 | 10/1982 | Mesek et al. . | |
| 4,496,360 | 1/1985 | Joffe et al. | 604/397 |

FOREIGN PATENT DOCUMENTS

| | | | |
|---|---|---|---|
| 0027303 | 4/1981 | European Pat. Off. . | |
| 0098512 | 6/1983 | European Pat. Off. | 128/290 |
| 0091412 | 10/1983 | European Pat. Off. | 604/385 |
| 8210000 | 8/1972 | Fed. Rep. of Germany . | |
| 2854792 | 6/1980 | Fed. Rep. of Germany . | |
| 1452841 | 10/1976 | United Kingdom . | |
| 2002073 | 2/1979 | United Kingdom . | |

OTHER PUBLICATIONS

Search Report in British Application 8504493 (May 7, 1985).
European Search Report in Application 85101777.2 (5 pages) Jul. 1, 1985.

*Primary Examiner*—John D. Yasko
*Assistant Examiner*—Sharon Rose
*Attorney, Agent, or Firm*—Paul A. Leipold; Thomas J. Connelly

[57] ABSTRACT

A sanitary napkin is provided with inwardly arcuate sides and elastic positioned centrally longitudinally along each of the sides and outward from the seal which attaches a fluid permeable cover directly to a fluid impermeable baffle. The elastic constricts the sides of the napkin to provide a cup-shaped profile with the bottom of the profile corresponding generally to the perineal area of the wearer.

3 Claims, 1 Drawing Sheet

SHAPED NAPKIN WITH ELASTICIZED EDGES

This is a continuation of co-pending application Ser. No. 581,945, filed on Feb. 21, 1984, now abandoned.

FIELD OF THE INVENTION

This application relates to a sanitary napkin and particularly to a sanitary napkin having inwardly arcuate sides.

BACKGROUND OF THE INVENTION

Sanitary napkins in use suffer from two major disfunctions. One of these is leakage. In most instances, leakage results not from saturation of the absorbent material, but rather fluid run off from the surface of the porous fluid permeable cover material prior to the penetration of the fluid through the cover and into the absorbent matrix. This may be due to a variety of factors, such as the nature of the fluid itself. Menses is a complex fluid which may be highly viscous and contains amongst other components cellular debris and a mucoidal fraction. Both the mucoidal fraction and the cellular debris tend to collect at the surface capillaries of the cover material and block the transmission of the more aqueous component into the absorbent.

Difficulties in this downward fluid transmission is heightened by the irregular capillary size and shape and even areas of complete lack of capillaries which can occur in the manufacturing processes associated with certain nonwovens. Fluid therefore strikes the surface of the cover and is blocked or the downward transmission retarded. Fluid then tends to spread along the surface and over the side edges resulting in napkin failure even though the bulk of the absorbent layer at either end, of the napkin has not even been wet. The other dysfunction which has only recently been identified relates to wetness of the cover. Because tabless sanitary napkins are designed to be attached to tight fitting undergarments, the surface of the nonwoven cover material is in direct contact with the perineal area, because of the tight fitting undergarments used by the wearer. Since the nonwoven cover materials are inherently nonwettable, there is a wet or damp surface feeling associated with them even when there is adequate downward transmission.

Attempts have been made to increase comfort of tabless sanitary napkins as well as to insure greater surface contact in the perineal area by providing napkins with inwardly arcuate sides. These napkins supposedly conform to the shape of the thighs adjacent the perineal area and therefore will suffer less distortion from movement by the wearer and it is theorized provide better fluid transmission downward into the absorbent component and due to the better surface interface between the perineal area and the cover.

In another type of sanitary garment, i.e., diapers, there is generally not the intimate contact between the crotch of the wearer and the containment garment. Diapers are, of course, of a vastly different configuration. Diapers, even though they include a fluid pervious nonwoven cover, an absorbent and a fluid impermeable baffle, are designed to be an undergarment with complete encircling of the legs and waist. Side leakage is prevented in diapers by the utilization of elastic completely around the leg area to provide a seal. U.S. Pat. No. 4,326,528 discloses a diaper which is arcuate in cross-sectional profile and constructed to form a containment pocket. U.S. Pat. No. 4,226,238 describes a rather complicated diaper construction in which a slightly elasticized central pouch is formed. U.S. Pat. No. 3,371,668 describes a sanitary napkin which utilizes elastic for certain constructional purposes. This type of seal is impossible to be obtained with a sanitary napkin which is not designed to be a garment with encircling means around the leg openings. European Pat. No. 0091412 discloses a sanitary napkin with elasticized edges, which due to its construction, features a raised bulky central area and side flaps.

SUMMARY OF THE INVENTION

This invention relates to a sanitary napkin of traditional components, i.e., fluid impermeable baffle, a fluid pervious cover, and an absorbent portion there between which forms a cup-shaped configuration with the bottom, i.e. deepest portion of the cup corresponding and generally to the perineal area of the wearer.

This is accomplished by forming a napkin with inwardly arcuate sides, attaching the fluid pervious cover directly to the fluid impervious baffle, at least in the area of the sides, and applying elastic to each of the sides outside of the seal line which attaches the cover to the baffle. When the elastic is relaxed it constrains the napkin to form a cup-shaped configuration with the central portion of the napkin forming the deepest part of the cup. This "bottom of the cup" corresponds generally to the perineal area and therefore the possibilities of direct contact between the perineal area and the cover are minimized particularly when the wearer is in a standing or reclining position. The configuration of the napkin allows the central portion to act as a reservoir with additional time for the fluid to penetrate the cover. Due to the presence of the elastic at the sides and the fact that the central portion receiving the fluid is lower than the sides, side leakage is virtually impossible.

Also because of the minimal amount of contact between the body of the wearer and the surface of the cover, the undesirable wet feeling associated with intimate contact is avoided.

DETAILED DESCRIPTION OF THE INVENTION AND DRAWINGS

The invention may be more readily understood by reference to the drawings in which.

Figure 1:
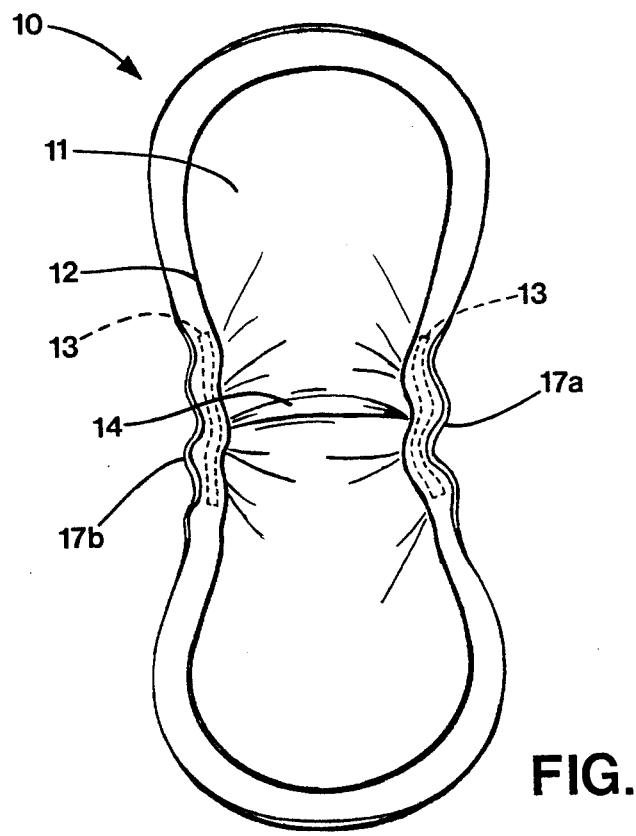
FIG. 1 is a plan view of the napkin and cross section.

As can be seen by reference to FIG. 1, the napkin 10 of this invention has generally inwardly arcuate sides 17a and 17b. A cover 11 is sealed inward from the outer edge of the napkin by seal line 12. This seal may be either by adhesive means or preferably a continuous or discontinuous ultrasonic band. Elastic elements 13 are added at the approximate center of each longitudinal side edge of a napkin outward of the seal line 12.

The napkin is essentially planar when the elastic is applied in a stretched condition and attached, e.g. by adhesive means. The elastic strips 13, when returning to their relaxed position, distort the planar configuration of the napkin by pulling the ends of the napkin upward toward each other and the sides of the napkin inward. This distortion forms the cup-like profile 14.

One particularly preferred method of introducing elastic is by utilizing an extrudable elastic which is extruded initially as a liquid and which upon cooling both is adhesive and is elastic. This eliminates the separate step of adhesively bonding strips of elastic to either side. An example of such a product is described in U.S. Pat. No. 4,259,220 assigned to H. B. Fuller Company in Saint Paul, Minn.

Figure 2:
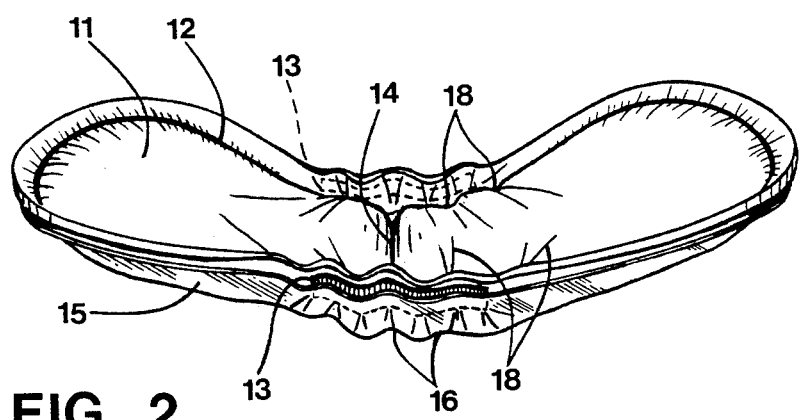
FIG. 2 is a side perspective view of a napkin which is partially turned toward the viewer.
Figure 3:
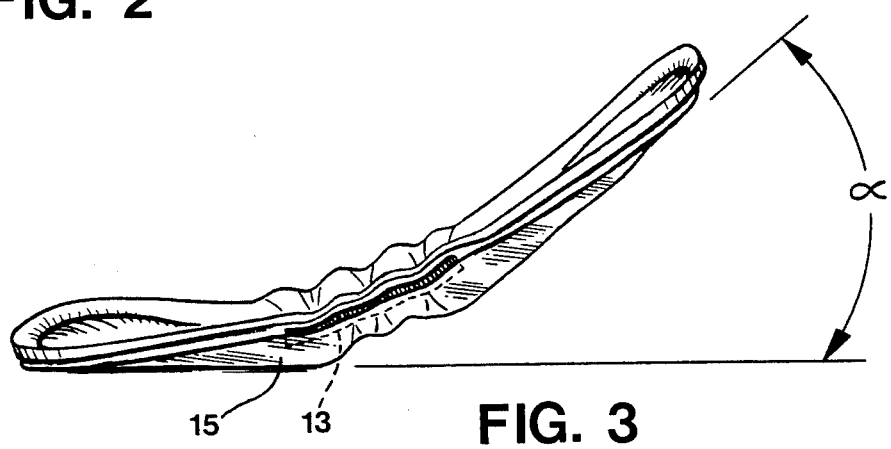
FIG. 3 is a side perspective view of the napkin according to this invention.

The general configuration of this napkin can more readily be seen by reference to FIG. 2 in which a baffle 15 is shown providing the outside of the cup and the cover 11 provides the inside surface. The bottom portion of the cup 14 is shown as a small fold. There are also constriction 16 shown along the central portion of the baffle 15 with corresponding constrictions 18 present along the central portion edge of the cover 11. The extent of the folds 16, 14, and 18 are dependent upon the width and length of the elastic, the stiffness of the absorbent layer (not shown) and the napkin as a whole, as well as the degree of elasticity of the elastic bands 13. These factors are balanced, so that, as shown in FIG. 3, the angle formed by the outer profile of the edge of the napkin with the plane upon which the napkin rests is between 30° and 90°. The benefits associated with this napkin when the angle is less than 30° essentially disappear and it is extremely difficult when the angle is greater than 90° to maintain the proper napkin configuration during use.

For purposes of comfort it is desired that the elastic width be controlled between 1/16 and 5/16 of an inch and currently preferred as a width of 3/16″. Bands much beyond 5/16″ tend to chafe and become uncomfortable for the wearer. It is also desirable that the elastic be inset at least 1/16″ from the side edges. If a self-adhering elastic is not employed, it may be necessary to provide another seal closer to the edge of the napkin although this seal need not be continuous. The reason for the second seal would be to minimize the exposure to the edges of the baffle and the cover which also could provide chafing. It has generally been found that it is necessary only to extend the elastic from 10-30% of the length of the side edges of the napkin, of course, this will vary depending upon the degree of elasticity, the stiffness and flexibility of the napkin, and other factors discussed above.

It has been found that the best configuration results from placing the elastic outside of an initial seal line, although some of the benefits of this invention may be obtained by placing the napkin exactly at or slightly inside of the seal line.

What is claimed is:

1. A sanitary napkin comprising a cup-shaped napkin having arcuate inwardly extending edges that form the deepest portion of the cup corresponding generally to the perineal area in the area of narrowest width and wherein (a) the cupping is such that the angle formed by the outer profile of the edge of the napkin with the plane upon which the napkin rests is between 30° and 90°, (b) said cupping is achieved by elastic extending from 10 to 30 percent of the length of the side edges of said napkin, (c) said cupping is achieved by elastic located at or exterior of the area where a fluid impermeable baffle and a fluid pervious cover are sealed together, (d) said napkin having a central portion which acts as a reservoir to provide additional time for fluid applied to said napkin to penetrate the cover, and (e) said napkin having an absorbent which has arcuate edges.

2. The napkin according to claim 1 wherein the width of the elastic is between 1/16″ and 5/16″.

3. The napkin of claim 1 wherein said elastic is inset at least 1/16″ from the side edges.

* * * * *